United States Patent [19]

Hajek et al.

[11] 4,404,379
[45] Sep. 13, 1983

[54] CYCLOAMINALS AND A PROCESS FOR THEIR PREPARATION

[75] Inventors: Manfred Hajek, Cologne; Kuno Wagner, Leverkusen; Walter Uerdingen, Bergisch-Gladbach; Wolfgang Wellner, Cologne, all of Fed. Rep. of Germany

[73] Assignee: Bayer Aktiengesellschaft, Leverkusen, Fed. Rep. of Germany

[21] Appl. No.: 935,439

[22] Filed: Aug. 21, 1978

[30] Foreign Application Priority Data

Sep. 1, 1977 [DE] Fed. Rep. of Germany ....... 2739313

[51] Int. Cl.³ .......................................... C07D 239/04
[52] U.S. Cl. ..................................... 544/231; 528/45; 528/73; 544/296; 544/335; 548/323; 548/336; 548/341; 260/239 BC
[58] Field of Search ...................... 544/231, 335, 296; 548/323; 260/239 BC

[56] References Cited

U.S. PATENT DOCUMENTS

| | | | |
|---|---|---|---|
| 3,591,590 | 6/1971 | Haug et al. | 544/231 |
| 3,661,923 | 5/1972 | Emmons et al. | 544/72 |
| 3,723,454 | 3/1973 | Ost et al. | 544/335 |
| 3,743,626 | 7/1973 | Emmons | 260/77.5 AQ |
| 3,778,439 | 12/1973 | Habermeier | 544/296 |
| 3,864,335 | 2/1975 | Emmons | 544/72 |
| 4,002,601 | 1/1977 | Hajek et al. | 544/71 |

OTHER PUBLICATIONS

Saunders et al., "Polyurethanes: Chemistry and Technology," Pt. I, 1962, pp. 76-79, 204-208.
Grant, *Hackh's Chemical Dictionary*, 4th Ed., 1969, McGraw-Hill, New York, pp. 331.

*Primary Examiner*—Nicholas S. Rizzo
*Assistant Examiner*—James H. Turnipseed
*Attorney, Agent, or Firm*—Gene Harsh; Lawrence S. Pope; Thomas W. Roy

[57] ABSTRACT

The present invention is concerned with a new class of compounds prepared by reacting cyclic aminals of the formula

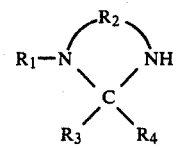

with polyisocyanates of the formula $R_5(NCO)_{m+n}$ to yield

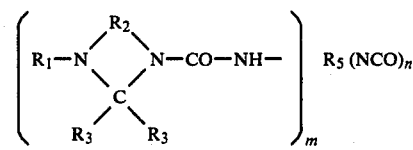

and with this process for obtaining said compounds, as well as the use of such compounds in polyurethane chemistry. If such compounds are free of isocyanates (n=0) they are useful as latent cross-linkers or hardeners activatable by heat or moisture. If such compounds carry free isocyanate groups (n=1 or 2) there are useful as synthetic resin precursors. In the above formulae m represents an integer of from 1 to 3, and
n represents 0, 1 or 2, and the sum of m+n is 2 or 3,
$R_1$ represents an aliphatic hydrocarbon group which is optionally cyano-substituted and which has from 1 to 6 carbon atoms, a cycloaliphatic hydrocarbon group having from 5-10 carbon atoms or an araliphatic hydrocarbon group having from 7-10 carbon atoms;
$R_2$ represents a divalent aliphatic hydrocarbon group having from 2 to 6 carbon atoms, at least two carbon atoms being situated between the two nitrogen atoms;
$R_3$ and $R_4$ are identical or different and represent hydrogen, aliphatic hydrocarbon groups having from 1 to 18 carbon atoms, cycloaliphatic hydrocarbon groups having from 5 to 10 carbon atoms or aromatic hydrocarbon groups having from 6 to 10 carbon atoms, or the two groups $R_3$ and $R_4$ together with the carbon atom of the heterocyclic ring may also form a 5-membered or 6-membered cycloaliphatic ring; and
$R_5$ represents an (m+n)-valent group such as that which can be obtained by the removal of m+n isocyanate groups from an (m+n)-valent polyisocyanate.

8 Claims, No Drawings

CYCLOAMINALS AND A PROCESS FOR THEIR PREPARATION

SUMMARY OF THE INVENTION

The present invention relates to compounds corresponding to the formula:

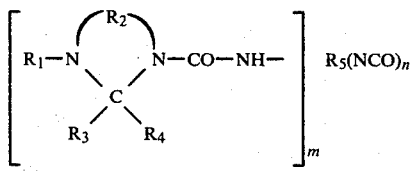

wherein
- m represents an integer of from 1 to 3 and
- n represents 0, 1 or 2 and the sum of m+n is 2 or 3,
- $R_1$ represents an aliphatic hydrocarbon group which is optionally cyano-substituted and which has from 1 to 6 carbon atoms, a cycloaliphatic hydrocarbon group having from 5–10 carbon atoms or an araliphatic hydrocarbon group having from 7–10 carbon atoms;
- $R_2$ represents a divalent aliphatic hydrocarbon group having from 2 to 6 carbon atoms, at least two carbon atoms being situated between the two nitrogen atoms;
- $R_3$ and $R_4$ are identical or different and represent hydrogen, aliphatic hydrocarbon groups having from 1 to 18 carbon atoms, cycloaliphatic hydrocarbon groups having from 5 to 10 carbon atoms or aromatic hydrocarbon groups having from 6 to 10 carbon atoms, or the two groups $R_3$ and $R_4$ together with the carbon atom of the heterocyclic ring may also form a 5-membered or 6-membered cycloaliphatic ring; and
- $R_5$ represents an (m+n)-valent group such as that which can be obtained by the removal of m+n isocyanate groups from an (m+n)-valent polyisocyanate.

The present invention also relates to a process for the preparation of these compounds, wherein cyclic aminals corresponding to the formula:

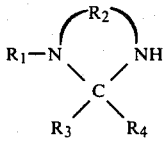

are reacted with polyisocyanates corresponding to the formula:

wherein $R_1$, $R_2$, $R_3$, $R_4$, $R_5$, m and n are defined as above.

The present invention also relates to the use of compounds corresponding to the first-mentioned formula which are free from isocyanate groups as cross-linking agents which can be activated by moisture and/or heat for the cross-linking of synthetic resin precursors which have free isocyanate groups or isocyanate groups which are blocked with known blocking agents for isocyanate groups.

Lastly, the present invention relates to the use of compounds corresponding to the first-mentioned formula which have free isocyanate groups as synthetic resin precursors which react under the influence of moisture and/or heat to form high molecular weight synthetic resins.

In these formulae and below, $R_1$, $R_2$, $R_3$, $R_4$, $R_5$, m and n are defined as above. Preferably,
- $R_1$ represents an aliphatic hydrocarbon group having from 1 to 3 carbon atoms which, if it has at least two carbon atoms, may have a cyano substituent in the 2-position, or it represents a cyclohexyl group.
- $R_2$ represents a dimethylene or trimethylene group,
- $R_3$ and $R_4$ represent, independently of each other, hydrogen, an aliphatic hydrocarbon group having from 1 to 3 carbon atoms, or, together with the carbon atom of the heterocyclic ring, a cyclohexyl group,
- $R_5$ represents a divalent group such as can be obtained by the removal of the isocyanate groups from hexamethylene diisocyanate, 2,4- and/or 2,6-diisocyanatotoluene, 4,4'-diisocyanatodiphenylmethane or 1-isocyanato-3,3,5-trimethyl-5-isocyanatomethylcyclohexane,
- n represents 0 or 1, and
- m represents 1 or 2, and the sum of n+m is 2.

BACKGROUND OF THE INVENTION

Polyamines are fundamentally interesting reaction components for the isocyanate polyaddition process because they give rise to products which contain the stable urea linkage. One disadvantage in this connection is the high reactivity of this class of compounds, which makes even ordinary mixing of the reactants difficult and completely prevents the preparation of mixtures having a long pot life or storage life. Many amines are even further limited in their use by their volatility and physiological action.

These disadvantages of this technically interesting class of substances can be obviated by using the cycloaminals according to the present invention.

DETAILED DESCRIPTION OF THE INVENTION

Mixtures of the cycloaminals according to the present invention with polyisocyanates are stable in storage in the absence of moisture. This is surprising since it is known that cyclic aminals such as, for example, N,N'-substituted imidazolidines (see H. Böhme, W. Pasche, Arch. Parmaz. 302 (1969) 2, 81–90) react with isocyanates by interposition reactions to form triazacycloheptanone derivatives. Cycloaminals are readily split by moisture giving rise, in addition to the carbonyl compound $R_3R_4C=O$, to an isocyanate-reactive compound having the following end groups:

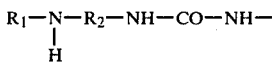

The cycloaminals which are free from isocyanate groups are thus potential reactants for organic polyisocyanates, and mixtures of such polycycloaminals with polyisocyanates therefore constitute systems which can be hardened by water, each cycloaminal group giving rise to only one secondary amino function since the second NH group forms part of a urea group and is therefore very slow to react with isocyanate groups. The functionality of the blocked amines according to the present invention is therefore exactly equal to the number of cycloaminal units in the molecule. The distance between the masked secondary amino groups, and the maximum functionality can be determined by suitable choice of the isocyanate derivative and these factors are therefore variable within wide limits and can be optimally adapted to the individual requirements of various applications.

The starting compounds used for the preparation of the compounds according to the present invention by the process according to the present invention may be N-substituted cyclic aminals corresponding to the general formula:

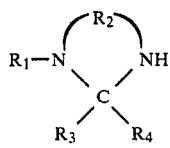

and these may be reacted with polyfunctional isocyanates corresponding to the following general formula:

$R_5(NCO)_{m+n}$

The cycloaminals required for the process according to the present invention may be prepared by a ring closing condensation of monosubstituted diamines corresponding to the formula:

with aldehydes or ketones corresponding to the general formula:

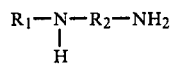

accompanied by the elimination of water, using known methods.

Particularly suitable N-monosubstituted diamines corresponding to the general formula:

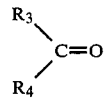

are derivatives of ethylene diamine, 1,2-propylene diamine, trimethylene diamine and tetramethylene diamine. In these diamines, the group $R_1$ may be, for example, a lower alkyl group such as a methyl, ethyl, propyl, i-propyl, n-butyl, i-butyl or t-butyl group. Monoaddition products of diamines corresponding to the following formula:

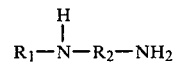

with activated double bond systems, e.g. derivatives of acrylic acid, such as acrylonitrile or methacrylonitrile, are also suitable.

The N-cyclohexyl, N-benzyl and N-phenyl derivatives of the above-mentioned diamines, for example, may also be used.

The following aldehydes and ketones are examples of suitable carbonyl compounds: formaldehyde, acetaldehyde, propionaldehyde, butyraldehyde, isobutyraldehyde, benzaldehyde, tetrahydrobenzaldehyde, acetone, methyl ethyl ketone, methyl propyl ketone, methyl isopropyl ketone, diethyl ketone, methyl butyl ketone, methyl isobutyl ketone, methyl-t-butyl ketone, diisobutyl ketone, cyclopentanone and cyclohexanone.

The compounds used as the polyisocyanate component $R_5$ $(NCO)_{m+n}$ may be aliphatic, cycloaliphatic, araliphatic, aromatic or heterocyclic polyisocyanates such as those described, for example, by W. Siefken in Justus Liebigs Annalen der Chemie, 562, pages 75 to 136, and J. H. Saunders and K. C. Frisch in *Polyurethanes Chemistry and Technology*, Part I Chemistry, 1962, pages 17–32, for example ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3- and -1,4-diisocyanate and any mixtures of these isomers, 1-isocyanato-3,3,5-trimethyl-5-isocyanatomethyl-cyclohexane (German Auslegeschrift No. 1,202,785), hexahydrotolylene-2,4-diisocyanate and -2,6-diisocyanate and mixtures of these isomers, hexahydrophenylene-1,3-diisocyanate and/or 1,4-diisocyanate, perhydrodiphenylmethane 2,4'-diisocyanate and/or 4,4'-diisocyanate, phenylene-1,3-diisocyanate and -1,4-diisocyanate, tolylene-2,4-diisocyanate and -2,6-diisocyanate and mixtures of these isomers, diphenylmethane-2,4'-diisocyanate and/or 4,4'-diisocyanate, naphthylene-1,5-diisocyanate, triphenylmethane-4,4',4''-triisocyanate, polyphenyl-polymethylene polyisocyanates which can be obtained by aniline/formaldehyde condensation followed by phosgenation and which have been described, for example, in British Patent Specification Nos. 874,430 and 848,671, perchlorinated aryl polyisocyanates such as those described, for example, in German Auslegeschrift No. 1,157,601, polyisocyanates having carbodiimide groups as described in German Pat. No. 1,092,007, diisocyanates of the kind described in U.S. Pat. No. 3,492,330, incorporated by reference herein, polyisocyanates containing allophanate groups as described e.g. in British Pat. No. 994,890, in Belgian Pat. No. 761,626 and in published Dutch Patent Application No. 7,102,524, polyisocyanates containing isocyanurate groups, e.g. as described in German Pat. Nos. 1,022,789; 1,222,067 and 1,027,394 and in German Offenlegungsschrift Nos. 1,929,034 and 2,004,048, polyisocyanates containing urethane groups as described e.g. in Belgian Pat. No. 752,261 or in U.S. Pat. No. 3,394,164, incorporated by reference herein, polyisocyanates containing acylated urea groups according to German Pat. No. 1,230,778, polyisocyanates containing biuret groups as described e.g. in German Pat. No. 1,101,394, in British Pat. No. 889,050 and in French Pat. No. 7,017,514, polyisocyanates prepared by telomerization reactions as described, for example, in Belgian Pat. No. 723,640, polyisocyanates having ester groups such as those mentioned, for example, in British Pat. Nos. 965,474 and 1,072,956, in U.S. Pat. No. 3,567,763, incorporated by reference herein, and in German Pat. No. 1,231,688 and reaction products of the above-mentioned isocyanates with acetals according to German Patent Specification No. 1,072,385. Any mixtures of the above-mentioned polyisocyanates may also be used.

The preferred polyisocyanates to be used in the process according to the present invention are those corresponding to the following formula:

$$R_5(NCO)_{m+n}$$

wherein $R_5$, m and n have the preferred meaning indicated above.

This means that the preferred isocyanate component to be used for the process according to the present invention consists of the preferred diisocyanates of polyurethane chemistry such as hexamethylene diisocyanate, 2,4- and/or 2,6-diisocyanatotoluene, 4,4'-diisocyanatodiphenylmethane or 1-isocyanato-3,3,5-trimethyl-5-isocyanatomethylcyclohexane (IPDI). Apart from such simple diisocyanates, isocyanate prepolymers prepared from such simple diisocyanates and subequivalent quantities of polyhydroxyl compounds of the type commonly used in polyurethane chemistry may also be used as the polyisocyanate component for the process according to the present invention. The known polyhydroxy polyethers or known polyhydroxy polyesters are preferably used for the preparation of these isocyanate prepolymers. The hydroxyl functionality of these polyhydroxyl compounds used for the preparation of the isocyanate prepolymers is preferably chosen so that the isocyanate prepolymers obtained have a valency of (m+n).

Polyesters with hydroxyl groups suitable for this purpose generally have a molecular weight of from about 600 to 6000, preferably from about 1000 to 4800, and consist of reaction products of polyhydric, preferably dihydric alcohols, optionally with the addition of trihydric alcohols, with subequivalent quantities of polybasic, preferably dibasic carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or unsaturated. The following are mentioned as examples: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid optionally mixed with monomeric fatty acids, dimethyl terephthalate and terephthalic acid-bis-glycol esters. The following are examples of suitable polyhydric alcohols: ethylene glycol, propylene glycol-(1,2) and -(1,3), butylene glycol-(1,4) and -(2,3), hexanediol-(1,6), octanediol-(1,8), neopentylglycol, 1,4-bis-hydroxymethylcyclohexane, 2-methyl-1,3-propanediol, glycerol, trimethylolpropane, hexanetriol-(1,2,6), butanetriol-(1,2,4), trimethylolethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may also contain a proportion of carboxyl end groups. Polyesters of lactones such as δ-caprolactone or hydroxycarboxylic acids such as ω-hydroxycaproic acid may also be used.

The polyhydroxypolyethers used generally have a molecular weight of from about 600 to 6000, preferably from about 1000 to 4800, and are prepared by, for example, the polymerization of epoxides such as ethylene oxide, propylene oxide, butylene oxide, tetrahydrofuran, styrene oxide or epichlorohydrin, either on their own, e.g. in the presence of boron trifluoride, or by the chemical addition of these epoxides, optionally as mixtures or successively, to starting components which have reactive hydrogen atoms, such as alcohols or amines, e.g. water, ethylene glycol, propylene glycol-(1,3) or -(1,2), trimethylolpropane, 4,4'-dihydroxydiphenylpropane, aniline, ammonia, ethanolamine or ethylene diamine. It is frequently preferred to use polyethers which contain predominantly (up to 90% by weight, based on all the hydroxyl groups present in the polyether) primary hydroxyl groups. Polyethers modified with vinyl polymers, e.g. the compounds obtained by the polymerizartion of styrene or acrylonitrile in the presence of polyethers (U.S. Pat. Nos. 3,383,351; 3,304,273; 3,523,093 and 3,110,695, all incorporated herein by reference, and German Pat. No. 1,152,536) are also suitable, as are also polybutadienes which have hydroxyl groups.

As the polyisocyanate component for the process according to the present invention there may, of course, also be used isocyanate prepolymers which have been prepared by the reaction of excess quantities of the polyisocyanates mentioned as examples, preferably diisocyanates, with isocyanate reactive compounds other than those mentioned as examples. Such other compounds containing isocyanate-reactive hydrogen atoms, which are also suitable in principle, include, for example, polythioethers such as the condensation products obtained by reacting thiodiglycol on its own and/or with other glycols, dicarboxylic acids, formaldehyde, aminocarboxylic acids or amino alcohols; polyacetals such as, for example, the compounds prepared from glycols and formaldehyde; polyhydroxypolycarbonates, e.g. the reaction products of glycols such as hexamethylene glycol with phosgene or diphenylcarbonate; polyester amides or polyamides having isocyanate-reactive hydrogen atoms in end positions, for example, the compounds which can be prepared from polybasic carboxylic acids or their anhydrides with aminoalcohols or diamines, or polyhydroxyl compounds already containing urethane or urea groups, or modified or unmodified natural polyols such as castor oil, carbohydrates or starch. Products of addition of alkylene oxides to phenolformaldehyde resins or to urea formaldehyde resins may also be used according to the present invention.

Representatives of these compounds which may be used according to the present invention have been described, for example, in High Polymers, Vol XVI, "Polyurethanes, Chemistry and Technology", by Saunders-Frish, Interscience Publishers, New York, London, Volume I, 1962, pages 32–42 and pages 44–54 and Volume II, 1964, pages 5–6 and 198–199, and in Kunststoff-Handbuch, Volume VII, Vieweg-Hochtlen, Carl-Hanser-Verlag, Munich, 1966, e.g. on pages 45–71.

The process according to the present invention is generally carried out by first introducing the cycloaminal into the reaction vessel and reacting it with the polyisocyanate in the form of an isocyanate addition reaction at temperatures of from about 10° C. to 80° C. The reaction may be carried out in the presence or absence of inert solvents such as acetone, methyl ethyl ketone, ethyl acetate, butyl acetate, toluene, xylene and/or solution petroleum hydrocarbons or mixtures of such solvents. In principle, it would be possible to reverse the sequence of mixing the reactants. The proportions of the reactants are generally chosen so that about 1 to 2 equivalents of NCO is available for each mol of cycloaminal.

When the ratio of (mol of cycloaminal):(equivalents of NCO) employed is 1:1, the process according to the present invention gives rise to products in which $n=0$, i.e. the latent hardeners for polyisocyanates mentioned above. When an excess of isocyanate is employed, products in which $n=1$ or 2, preferably 1 are obtained. These products are already moisture hardening synthetic resin precursors and by further reaction with compounds containing isocyanate-reactive groups they may be converted into compounds according to the present invention in which $n=0$, which latter compounds substantially correspond in their chemical constitution to those compounds according to the present invention which are obtained when the appropriate isocyanate prepolymers are used. Thus, for example, instead of using isocyanate prepolymers as the polyisocyanate component, the process according to the present invention may first be carried out with a low molecular weight diisocyanate corresponding to the isocyanate prepolymer, using an excess of this diisocyanate in order that the resulting reaction product which contains isocyanate groups may subsequently be modified with that compound corresponding to the NCO prepolymer which has isocyanate-reactive hydrogen atoms. According to another variation of carrying out the process of the present invention, a low molecular weight polyisocyanate, preferably a diisocyanate of the type indicated as an example, is directly reacted with a mixture of cycloaminal and compounds which have isocyanate-reactive hydrogen atoms. For preparing compounds according to the present invention which are free from isocyanate groups, it may also be advantageous to use a slight excess of isocyanate in order to compensate for any traces of moisture present in the cycloaminal. The process according to the present invention may also be carried out using a large excess of cycloaminal (greater than the above-mentioned ratio of 1:1). The unreacted cycloaminal may then be removed, for example by thin layer distillation, or the excess cycloaminal may be left in the reaction mixture since the unreacted cycloaminal may function as a low molecular weight, partially blocked cross-linking agent and its presence does not interfere in certain fields of application of the compounds according to the present invention.

Particularly preferred compounds according to the present invention are those which do not contain any free isocyanate groups and which are substantially inert towards isocyanate groups at room temperature and in the absence of moisture but are reactive with isocyanate groups under the influence of moisture and/or heat. As already explained above, when the products of the process according to the present invention are activated by moisture, hydrolytic decomposition of the aminal ring takes place with liberation of secondary amino groups which are highly reactive towards isocyanate groups. When the compounds according to the present invention are activated solely by heat without any access of moisture, the cross-linking reactions which take place are very probably of a different nature and their mechanism has not yet been fully clarified. It is established, however, that mixtures of synthetic resin precursors which contain isocyanate groups and compounds according to the present invention can be converted into high molecular weight synthetic resins by the action of heat alone in the absence of moisture, for example by being heated to temperatures of from about 100° C. to 160° C. with the exclusion of air and moisture.

The preferred compounds according to the present invention, which are free from isocyanate groups, are preferably prepared exclusively from the simple organic diisocyanates already mentioned as examples. In order to produce compounds according to the present invention which contain isocyanate groups, it is preferable to use isocyanate prepolymers through which the higher molecular weight hydroxyl compounds mentioned as examples are incorporated at the same time so that the reaction products themselves constitute true oligomeric synthetic resin precursors which react to form high molecular weight synthetic resins under the influence of moisture and/or heat. The compounds according to the present invention which are free from isocyanate groups are not only suitable latent cross-linking agents for synthetic resin precursors which contain isocyanate groups (for example, the isocyanate prepolymers mentioned above as examples) but may also be added as latent chain lengthening agents or cross-linking agents to reactive systems based on organic polyisocyanates of the type mentioned as examples and organic compounds with isocyanate-reactive hydrogen atoms mentioned above as examples. It is surprisingly found that when they are added to such reactive systems, they also have the effect of increasing the pot life and lowering the drying time of the systems. In such systems, the isocyanate groups are generally present in a molar excess of from about 1.05 to 1.4 times the active hydrogen atoms present in the component which has isocyanate-reactive groups, and the compound according to the present invention is present in a quantity which is at least about 0.8 times equivalent to this isocyanate excess.

The reactive systems described here may contain inert additives such as solvents, plasticizers, flame-retarding agents, fillers, deaerating agents, flow aids or pigments to adapt them to the particular purpose for which they are to be used. The reactive systems described are suitable for the production of lacquers, coatings or sealing materials or fillers for numerous substrates such as wood, paper, textiles, leather, glass, stone, concrete or metal. They are particularly suitable for use in the building industry and the motor car industry. Depending on the purpose for which they are required, the reactive systems may be applied by brush coating, spraying, trowelling, casting or knife coating.

EXAMPLES

EXAMPLE 1

N-methyl-hexahydropyrimidine

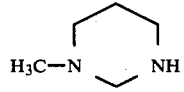

528 g of N-methyl-1,3-propanediamine is added slowly, dropwise, to a suspension of 198 g of paraformaldehyde in 700 ml of cyclohexane at 60° C. The water produced in the reaction is removed by boiling under reflux, using a water separator. After filtration to remove insoluble constituents, the filtrate is distilled over a 30 cm Vigreux column. 455 g of N-methyl-hexahydropypyrimidine, boiling at from 130° to 138° C. under normal pressure, are obtained.

EXAMPLE 2

1-methyl-2-(1-methylethyl)-hexahydropyrimidine

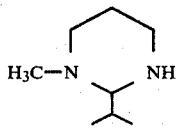

530 g of N-methyl-1,3-diaminopropane are slowly added dropwise to a mixture of 650 ml of isobutyraldehyde and 400 ml of cyclohexane cooled with ice. When the exothermic reaction has died down, the reaction mixture is boiled under reflux on a water separator until approximately 108 ml of water have been separated. Cyclohexane and isobutyraldehyde are distilled off at reduced pressure. Fractional distillation of the residue (b.p.$_{15}$: 68° to 75° C.) yields 680 g of 1-methyl-2-isopropylhexahydropyrimidine.

EXAMPLE 3

N-cyclohexyl-hexahydropyrimidine

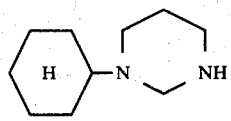

312 g of N-cyclohexyl-1,3-propanediamine are slowly added dropwise at 60° C. to a suspension of 66 g of paraformaldehyde in 200 ml of cyclohexane. The water of reaction is then removed by boiling under reflux on a water separator. Insoluble constituents are removed by filtration and the filtrate is subjected to fractional distillation. 248 g of N-cyclohexyl-hexahydropyrimidine boiling at from 87° to 91° C. at 0.3 mbar are obtained.

EXAMPLE 4

N-(6-isocyanato-1,6-hexanediyl)-3-methylhexahydropyrimidine-1-carboxamide 100 g of N-methyl-hexahydropyrimidine are slowly added dropwise to 336 g of hexamethylene diisocyanate at room temperature. The mixture is then stirred for a further 3 hours. 250 ml of cyclohexane are then added and the mixture is stirred at room temperature for one hour. The cyclohexane phase is separated off and the process of purification is repeated three times, each time with 250 ml of cyclohexane. After removal of the solvent, the product is freed from residues of cyclohexane by thin layer distillation at 100° C. and at 15 mbar. The product contains less than 0.4% of free diisocyanate and consists preferentially of the following monoisocyanate:

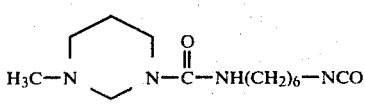

EXAMPLE 5

N-(5-isocyanato-1,3,3-trimethyl-1-cyclohexylmethyl)-3-methyl-2-(1-methylethyl)-hexahydropyrimidine-1-carboxamide

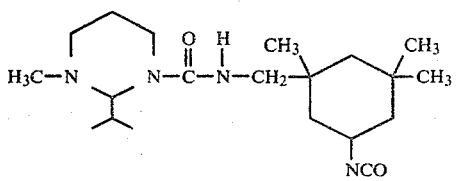

142 g of N-methyl-2-isopropyl-hexahydropyrimidine are slowly added dropwise to 888 g of isophorone diisocyanate at room temperature. The mixture is then stirred for 6 hours and most of the excess diisocyanate is removed by thin layer distillation (at 160° C. and at 0.1 mbar). The residue is dissolved in toluene, precipitated by the addition of cyclohexane, suction filtered, washed with cyclohexane and dried. Approximately 300 g of a product preferentially consisting of the 1:1 addition product of isophorone diisocyanate and the hexahydropyrimidine derivative (mp.: 180°-192° C.) are obtained.

EXAMPLE 6

A modified polyol 108 g of the hexahydropyrimidine isocyanate which has been prepared as described in Example 4 and 0.2 g of dibutyl tin dilaurate are added to 627 g of a polyester which has been prepared from phthalic acid, trimethylolpropane, α-ethyl-hexanedicarboxylic acid and 2-ethylhexane-1,3-diol and which has a hydroxyl content of 8.1%. The reaction is carried out at temperatures of around 40° C. A modified polyester polyol is obtained which contains hydroxyl and hexahydropyrimidine end groups side by side. The product has a hydroxyl number of 256 and an acid number of 11.6. For practical reasons, the NH functions produced by hydrolysis are included in the hydroxyl number.

EXAMPLE 7

A prepolymer containing isocyanate end groups and hexahydropyrimidine end groups 72 g of N-methyl-2-isopropyl-hexahydropyrimidine are slowly added at a temperature of from 30° to 40° C. to 1150 g of an isocyanate prepolymer which has an isocyanate content of 3.8% and which has been prepared by the reaction of isophorone diisocyanate with a polyether based on propylene oxide, the polyether being started on propylene glycol and having a hydroxyl number of 56. The reaction mixture is then stirred for 8 hours at room temperature.

A prepolymer which can be hardened by moisture and/or heat is obtained.

EXAMPLE 8

A prepolymer containing hexahydropyrimidine end groups 150 g of N-methyl-2-isopropyl-hexahydropyrimidine are slowly added at room temperatures to 1100 g of an isocyanate prepolymer which has an isocyanate content of 3.8% and which has been obtained by the action of tolylene-2,4-diisocyanate with a polyether based on propylene oxide which has been started on propylene glycol and has a hydroxyl number of 56. The reaction mixture is then stirred at the same temperature until the isocyanate band in the IR spectrum has disappeared.

The product has a viscosity of 120,000 mPas (25° C.) and an NH equivalent weight, determined by titration, of 1280.

EXAMPLE 9

N,N'-(1,6-hexanediyl)-bis-[3-(2-cyanoethyl)-2-(1-methyl-ethyl)-1-imidazolidine-carboxamide]

226 g of N-(2-cyanoethyl)-ethylenediamine are slowly added dropwise to a mixture of 144 g of isobutyraldehyde in 400 ml of cyclohexane. The temperature is kept below 30° C. by cooling. When all the diamine has been added, the reaction mixture is boiled under reflux on a water separator until approximately 30 ml of water have been removed. The solvent is then distilled off. 168 g of hexamethylene diisocyanate are slowly added to the crude imidazolidine at temperatures of between 30° and 40° C. with cooling. A viscous, light yellow product is obtained, which preferentially corresponds to the following formula:

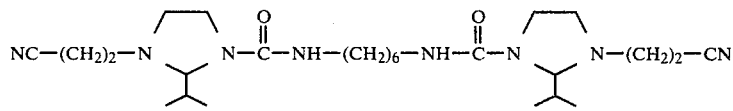

EXAMPLE 10

N,N'-(1,6-hexanediyl)-bis-[3-methyl-2-(1-methylethyl)-1-hexahydropyrimidine-carboxamide]

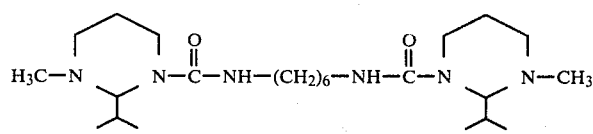

A mixture of 84 g of hexamethylene diisocyanate and 100 g of ethyl acetate is slowly added at temperatures of from 25° to 35° C. to 142 g of N-methyl-2-isopropylhexahydropyrimidine

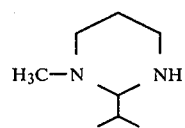

in 150 ml of ethyl acetate. Stirring is continued for 8 hours at room temperature after the reaction has been completed and the ester is finally removed on a rotary evaporator at 100° C. and at 25 mbar.

EXAMPLE 11

N,N'-(1,6-hexanediyl)-bis-(3-methyl-1-hexahydropyrimidine-carboxamide)

168 g of hexamethylenediisocyanate in 150 ml of ethyl acetate are slowly added to a mixture of 224 g of N-methylhexahydropyrimidine and 150 ml of ethyl acetate cooled to temperatures of from 15° to 20° C. Stirring is continued at room temperature after all the diisocyanate has been added until the isocyanate band in the IR spectrum has disappeared (after about 2 hours). The solvent is removed on a thin layer evaporator at 110° C. under a vacuum produced by a water jet pump. The viscous product preferentially consists of the following bis-hexahydropyrimidine derivative:

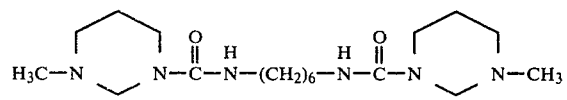

The following abbreviations are used in the Examples which follow:

Product 1 = polyacrylate resin based on styrene, butyl acrylate and hydroxypropyl acrylate, containing 4.8% by weight hydroxyl.

Product 2 = N,N'-(1,6-hexanediyl)-bis-[3-methyl-2-(1-methylethyl)-1-hexahydropyrimidine-carboxamide]

Product 3 = N,N'-(1,6-hexanediyl)-bis-(3-methyl-1-hexahydropyrimidine-carboxamide)

Product 4 = commercial deaerating agent based on polyacrylate resin (MODAFLOW, Monsanto)

Product 5 = commercial levelling agent based on silicone oil (BAYSILONÖL, Bayer AG, Germany)

Product 6 = biuret group-containing polyisocyanate based on hexamethylene diisocyanate, containing 23.5% by weight of NCO.

EXAMPLE 12

100.0 g of an isocyanate prepolymer prepared from a polyol mixture consisting of 1 mol of a linear polypropylene glycol having a molecular weight of 2000 and 0.4 mol of a propoxylated trimethylpropane having a molecular weight of 2000 and excess 3,3,5-trimethyl-5-isocyanato-methyl-cyclohexylisocyanate (NCO content: 4.0%, viscosity at 20° C.: about 7500 mPas) and 27 g of a product 2 are mixed together after the addition of 1.0 g of oleic acid.

Thick coatings form a skin within 2 hours at room temperature and a relative humidity of 50% and harden to form elastic coverings.

The binder system mentioned above can be stored for more than 10 days at 50° C.

EXAMPLE 13

Preparation of a sealing compound which can be hardened by moisture 100.0 g of the isocyanate prepolymer described in Example 12
150.0 g of alkylsulphonic acid ester ($C_{15}H_{31}$—$SO_3$—$C_6H_5$) (plasticizer)
75.0 g of chalk powder
18.0 g of highly disperse silica 5.0 g of zeolite powder (molecular sieve)
5.0 g of titanium dioxide
0.2 g of carbon black
10.0 g of xylene
25.0 g of product 2.

The sealing compound forms a skin after about 4 hours at room temperature and 50% relative humidity and hardens through a thickness of 1 to 2 mm per day. Shore hardness A of hardened material: about 20. The mixture can be stored for over three months at 20° C.

EXAMPLE 14

(Comparison)

The composition of component A is as follows:

| | |
|---|---|
| Product 1, 80% in EGA* | 125.0 parts by weight |
| Product 4, 10% in EGA | 0.7 parts by weight |
| Product 5, 10% in xylene | 1.4 parts by weight |
| Zinc octoate, 10% in xylene | 2.9 parts by weight |
| EGA | 37.2 parts by weight |
| Xylene | 37.1 parts by weight |
| | 204.3 parts by weight |
| Component B | |
| EGA/xylene (1:1) | 13.7 parts by weight |
| Product 6, 100% | 44.1 parts by weight |
| | 57.8 parts by weight |

*Ethylene glycol monoethyl ether acetate
Pot life in closed vessel at 20° C.: about 14 hours 204.3 g of component A are intimately mixed with 57.8 of component B and the mixture is sprayed with a flow cup gun to form a film approximately 80 μm in thickness when wet.

The following physical drying values and film properties were obtained:

| | |
|---|---|
| Drying according to DIN 53150 | |
| Drying stage 1: | about 7 hours |
| Vibration experiments with pendulum apparatus DIN 53 157 | |
| (1.) after 1 day's storage at 23° C.: | about 40 sec. |
| (2.) after 30 minutes at 80° C.: | about 125 sec. |
| (3.) after 12 hours at 70° C.: | about 185 sec. |

EXAMPLE 15

The composition of component A is as follows:

| | |
|---|---|
| Product 1, 80% in EGA | 100.0 parts by weight |
| Product 3, 100% | 20.0 parts by weight |
| Product 4, 10% in EGA | 0.8 parts by weight |
| Product 5, 10% in xylene | 1.5 parts by weight |
| Zinc octoate, 10% in xylene | 3.1 parts by weight |
| EGA | 38.3 parts by weight |
| xylene | 38.3 parts by weight |
| | 202.0 parts by weight |
| Component B | |
| Product 6, 100% | 54.5 parts by weight |
| EGA/xylene (1:1) | 17.1 parts by weight |
| | 71.6 parts by weight. |

202.0 g of component A are intimately mixed with 71.6 g of component B and sprayed with a flow cup gun to form a film about 80 μm in thickness when wet.

The following physical drying values and film properties were determined:

| | |
|---|---|
| Drying according to DIN 53150 | |
| Drying stage 1: | about 4 hours |

-continued

| | |
|---|---|
| Vibration tests with pendulum apparatus DIN 53157 | |
| (1.) after 1 day's storage at 23° C.: | about 67 sec. |
| (2.) after 30 minutes at 80° C.: | about 143 sec. |
| (3.) after 12 hours at 70° C.: | about 186 sec. |
| Pot life until product gels in closed vessel at 20° C.: | about 25 hours. |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds corresponding to the following formula:

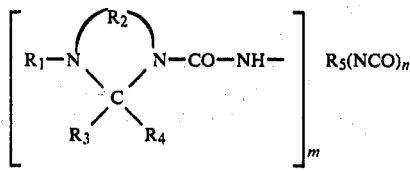

wherein
m represents an integer of from 1 to 3 and
n represents 0, 1 or 2 and the sum of m+n is 2 or 3;
$R_1$ represents an aliphatic hydrocarbon group which is optionally cyano-substituted and which has from 1 to 6 carbon atoms, a cycloaliphatic hydrocarbon group having from 5 to 10 carbon atoms or an araliphatic hydrocarbon group having from 7 to 10 carbon atoms;
$R_2$ represents a divalent aliphatic hydrocarbon group having from 2 to 6 carbon atoms, at least two carbon atoms being arranged between the two nitrogen atoms;
$R_3$ and $R_4$ are identical or different and represent hydrogen, aliphatic hydrocarbon groups having from 1 to 18 carbon atoms, cycloaliphatic hydrocarbon groups having from 5 to 10 carbon atoms or aromatic hydrocarbon groups having from 6 to 10 carbon atoms or the two groups $R_3$ and $R_4$ together with the carbon atom of the heterocyclic ring may form a 5-membered or 6-membered cycloaliphatic ring;
$R_5$ represents the (m+n)-valent group obtained by the removal of m+n isocyanate groups from an (m+n)-valent polyisocyanate.

2. A process for the preparation of compounds according to claim 1, wherein the cyclic aminals corresponding to the following formula:

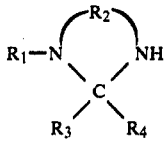

are reacted with polyisocyanates corresponding to the formula:

wherein $R_1$, $R_2$, $R_3$, $R_4$, $R_5$, m and n are defined as in claim 1.

3. The compounds of claim 1 wherein $R_1$ represents an aliphatic hydrocarbon group having from 1 to 3 carbon atoms which, if it has at least two carbon atoms, may have a cyano substituent in the 2-position, or it represents a cyclohexyl group, $R_2$ represents a dimethylene or trimethylene group, $R_3$ and $R_4$ represent, independently of each other, hydrogen, an aliphatic hydrocarbon group having from 1 to 3 carbon atoms, or, together with the carbon atom of the heterocyclic ring, a cyclohexyl group, $R_5$ represents the divalent group obtained by the removal of the isocyanate groups from hexamethylene diisocyanate, 2,4- and/or 2,6-diisocyanatotoluene, 4,4'-diisocyanatodiphenylmethane or 1-isocyanato-3,3,5-trimethyl-5-isocyanatomethyl-cyclohexane, n represents 0 or 1, and m represents 1 or 2, and the sum of n+m is 2.

4. A process for the preparation of the cycloaminals of claim 1 comprising reacting a cyclic aminal of the formula:

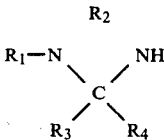

wherein $R_1$, $R_2$, $R_3$ and $R_4$ are as defined in claim 3 with an isocyanate selected from the group consisting of 2,4- and/or 2,6-diisocyanatotoluene, 4,4'-diisocyanatodiphenyl methane and 1-isocyanato-3,3,5-trimethyl-5-isocyanato methyl cyclohexane at about 10° to 80° C. with subsequent separation of any unreacted cyclic aminal.

5. The process of claim 2 wherein the polyisocyanate is the reaction product of a monomeric diisocyanate and a deficient amount of a dihydroxy polyol.

6. The process of claim 2 wherein an excess of polyisocyanate is used.

7. The process of claim 2 wherein less than an equivalent of polyisocyanate is used.

8. The process of claim 2 wherein the cyclic aminal to isocyanate group ratio is about 1:1.

* * * * *